United States Patent [19]

Watanabe et al.

[11] 4,414,331

[45] Nov. 8, 1983

[54] PROCESS FOR PRODUCING A HIGHLY CONCENTRATED AQUEOUS ACRYLAMIDE SOLUTION BY MEANS OF MICROORGANISMS

[75] Inventors: Ichiro Watanabe; Yoshiaki Satoh; Yasumasa Yamaguchi, all of Yokohama, Japan

[73] Assignee: Nitto Chemical Industry Co., Ltd., Tokyo, Japan

[21] Appl. No.: 160,792

[22] Filed: Jun. 19, 1980

[30] Foreign Application Priority Data

Jun. 19, 1979 [JP] Japan .................................. 54-76351

[51] Int. Cl.³ ..................... C12P 13/02; C12N 11/04; C12R 1/00; C12R 1/07; C12R 1/13; C12R 1/265; C12R 1/365; C12R 1/15
[52] U.S. Cl. .................................... 435/129; 435/182; 435/813; 435/819; 435/822; 435/832; 435/840; 435/843; 435/859; 435/872
[58] Field of Search ............... 435/129, 177, 182, 813, 435/819, 832, 840, 843, 859, 872, 244, 822

[56] References Cited

U.S. PATENT DOCUMENTS

| | | | |
|---|---|---|---|
| 3,389,567 | 6/1968 | Bevarly et al. | 426/524 |
| 3,624,154 | 11/1971 | Robbins et al. | 260/561 N |
| 4,001,081 | 1/1977 | Commeyras et al. | 435/129 |
| 4,248,968 | 2/1981 | Watanabe et al. | 435/129 |

*Primary Examiner*—Esther M. Kepplinger
*Attorney, Agent, or Firm*—Sughrue, Mion, Zinn, Macpeak and Seas

[57] ABSTRACT

A process for producing acrylamide from acrylonitrile by utilizing a microorganism or enzyme capable of hydrating acrylonitrile into acrylamide in the form of a highly concentrated aqueous solution of acrylamide which comprises bringing acrylonitrile in contact with the microorganism or enzyme in an aqueous medium at a pH of from 6 to 10, at a temperature of from the freezing point to 50° C., and under such conditions that the concentration of acrylamide in the reaction solution after the completion of the reaction is from 5% by weight to less than 20% by weight, and concentrating the resulting reaction solution; this invention further includes an embodiment wherein the reaction solution is concentrated by cooling the reaction solution after the reaction to from −4° C. to −9° C. to crystallize ice, separating the ice, and using the ice so separated for cooling during the hydration reaction. In addition, this invention includes an embodiment wherein the concentrated solution obtained by the above embodiment is further concentrated by evaporating the water contained in the concentrated solution.

11 Claims, 1 Drawing Figure

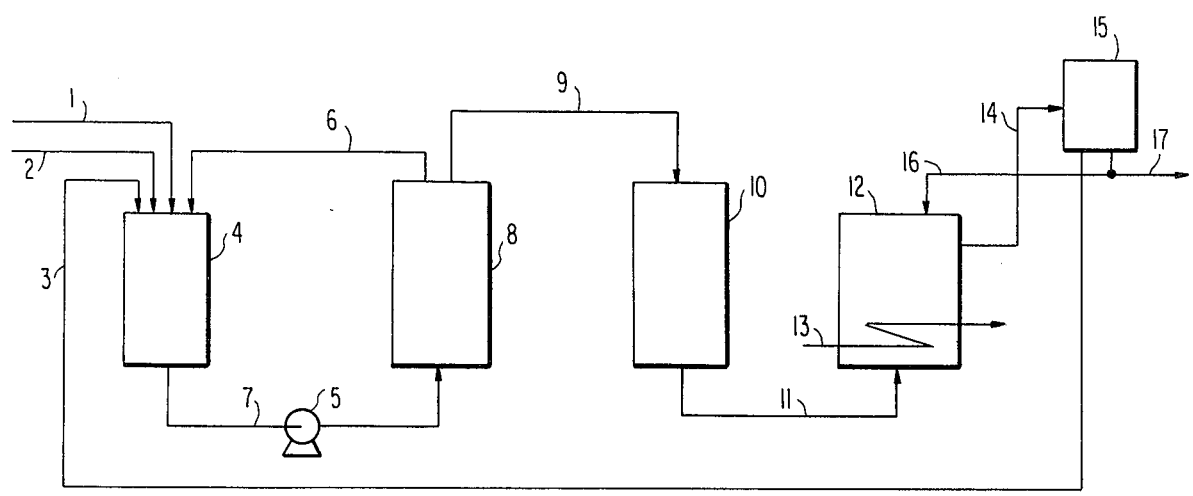

PROCESS FOR PRODUCING A HIGHLY CONCENTRATED AQUEOUS ACRYLAMIDE SOLUTION BY MEANS OF MICROORGANISMS

BACKGROUND OF THE INVENTION

1. Field of the Invention

This invention relates to an improved process for the production of a high concentrated acrylamide aqueous solution by biological hydration of acrylonitrile.

2. Description of the Prior Art

For the production of acrylamide, catalytic hydration methods have hitherto been known in which acrylonitrile is reacted with water in the presence of a catalyst, such as a copper-based catalyst, to produce acrylamide.

This catalytic hydration method, however, has disadvantages in that the preparation of such a catalyst is complicated, the reaction temperature (generally as high as 80° C. to 140° C.) can cause side-reactions such as polymerization, and in that by-products formed by such side-reactions and impurities eluted from the catalyst contaminate the product acrylamide, reducing the quality thereof and making it difficult to produce high molecular weight polymers of acrylamide. For the removal of such impurities, expensive purification techniques using active carbon, cation exchange resins, anion exchange resins, etc. are required.

Recently a process for producing acrylamide from acrylonitrile by the enzyme reaction using microorganisms belonging to the genera Bacillus, Bacteridium in the sense of Prévot, Micrococcus and Brevibacterium in the sense of Bergey has been disclosed, in U.S. Pat. No. 4,001,081, and another process has also been proposed for the production of acrylamide from acrylonitrile by use of microorganisms belonging to the genera Corynebacterium and Norcardia, as described in Japanese Patent Publication (OPI) No. 129190/79 (The term "OPI" as used herein refers to a "published unexamined Japanese patent application".).

SUMMARY OF THE INVENTION

As a result of investigations to produce acrylamide by the hydration of acrylonitrile using microorganisms, it has now been found that an aqueous solution of acrylamide of a high concentration and high quality can be efficiently produced by the hydration of acrylonitrile under specific conditions followed by the concentration of the resulting reaction solution.

This invention, therefore, provides a process for producing acrylamide by the hydration of acrylonitrile utilizing a microorganism or enzyme capable of hydrating acrylonitrile to form acrylamide, in which process acrylonitrile is contacted with the microorganism or enzyme in an aqueous medium at a pH of from 6 to 10 and a temperature of from the freezing point to 50° C. and under such conditions that the concentration of acrylamide in the reaction solution after completion of the reaction is in a range of from 5% by weight to less than 20% by weight to effect the hydration of acrylonitrile, and then the reaction solution thus-obtained is concentrated.

The acrylamide aqueous solution obtained by the process of this invention can be used as is a starting material for the production of various polymers without being subjected to any further purification to obtain polymers with high molecular weights and good performance characteristics, which have not been attained by conventional methods.

BRIEF DESCRIPTION OF THE DRAWING

The FIGURE is a diagram schematically showing one embodiment of the invention.

DETAILED DESCRIPTION OF THE INVENTION

Any microorganism capable of hydrolyzing acrylonitrile into acrylamide can be used in this invention, independently of the classification to which it belongs. For example, microorganisms belonging to the genera Bacillus, Bacteridium in the sense of Prevot, Micrococcus and Brevibacterium in the sense of Bergey, as described in U.S. Pat. No. 4,001,081 and to the genera Corynebacterium and Nocardia, as described in Japanese Patent Publication (OPI) No. 129190/1979, etc. can be used.

Preferred microorganisms are, for example, Strain N-771 (deposited in the Fermentation Research Institute, Japan, under the accession number of FERM-P No. 4445) and Strain No. 774 (FERM-P No. 4446), each belonging to the genus Corynebacterium, and Strain N-775 (FERM-P No. 4447) belonging to the genus Nocardia, as described in Japanese Patent Publication (OPI) No. 129190/1979.

While such microorganism can be used as is in the hydration reaction, it is preferred to immobilize the microorganism prior to the use thereof for convenience of handling. The immobilization can be carried out by any known method. Of these known methods, the polyacrylamide based gel entrapping method as described in Japanese Patent Publication (OPI) No. 143593/1979 is preferred.

When an enzyme is used, an enzyme solution can be extracted from the microorganism by, for example, a supersonic method, a freezing and thawing method, a lysozyme method, etc. is, if necessary, purified and immobilized. This immobilization can also be carried out by any known method. Preferred among these known methods is an ion bonding method in which the enzyme is bonded onto granular solid of ion exchange materials, such as porous anion exchange resins and diethylaminoethyl cellulose and deposited thereon (for instance, as shown in *IMOBILIZED ENZYME* published by kodansha on Mar. 20, 1975.).

The quality of acrylamide obtained by the hydration reaction will vary depending upon the concentration of the acrylamide, the temperature, the pH value, etc. during the hydration reaction. In particular, when the concentration of acrylamide exceeds 20% by weight during the hydration reaction, the quality of the acrylamide product is suddenly decreased. It is therefore necessary to control the reaction conditions so that the concentration of acrylamide after the reaction be less than 20% by weight, and preferably 15% by weight or less. The lower limit of the concentration of acrylamide is determined by the economic standpoint. It is usually about 5% by weight.

The reaction temperature can be raised to as high as 50° C. However, since the quality tends to lower and the reduction in the enzyme activity is accelerated as the reaction temperature rises, it is preferably 30° C. or less and more preferably 15° C. or less. The lower limit of the reaction temperature is the freezing point of the reaction system at which the reaction handling is still possible. At such low temperatures, the microorganisms and enzymes as described above possess sufficient activity. Thus it is preferred to conduct the reaction at a temperature from the freezing point of the reaction solution to 30° C., and more preferably at a temperature from the freezing point to 15° C.

The pH is maintained in the range of from 6 to 10, and preferably from 7 to 9. The pH range is chosen so that the microorganism fully exhibits its hydration activity of acrylonitrile and the contamination with impurities resulting from the formation of by-products such as acrylic acid and the reduction in the yield of acrylamide are prevented.

Various methods can be employed for the concentration of the reaction solution obtained by the hydration reaction. Considering that the temperature of the hydration reaction of this invention is lower by 10° C. or more than that in the catalytic hydration method, it is preferred in this invention to employ a method wherein the concentration of the reaction solution is carried out by cooling the reaction solution to precipitate ice containing substantially no acrylamide and to separate it from the reaction solution (this method is hereinafter referred to as a freezing concentrating method) because the energy required for the concentration can be saved.

In particular, when this freezing concentration method is combined with the hydration reaction which is carried out at 30° C. or less, and preferably at 15° C. or less, the ice obtained by the freezing concentration can be used for the cooling of the reaction solution during the hydration reaction, and thus the energy required for the reaction and concentration can be greatly reduced. Moreover, the enzyme activity during the hydration reaction can stably be maintained for extended periods of time. Furthermore, since both the reaction and concentration are carried out at low temperatures, the formation of by-products and the decomposition, polymerization, modification, etc. of these by-products and acrylamide do not occur to any significant extent during the reaction and concentration steps, thus leading to the production of a high quality product in high yields.

In contrast, when a reaction solution obtained by the catalytic hydration method is subjected to the freezing concentration method, a relatively large quantity of energy is required for the cooling, since the catalytic hydration method is carried out at high temperatures. Furthermore, as high a quality product cannot be obtained by the catalytic method.

In another aspect of this invention, the concentration of the reaction solution can be achieved by evaporating water contained in the reaction solution at atmospheric pressure or under reduced pressure conditions. This method can advantageously be employed when the reaction solution after the freezing concentration is desired to be further concentrated.

Since concentration by heating is carried out at high temperatures, the quality of the product is generally reduced using such a technique. Where a reaction solution obtained by the catalytic hydration method is concentrated by heating, the quality of the product is further lowered, whereas where the reaction solution obtained by this invention is concentrated by heating, substantially no reduction in quality is observed. This is believed to be due to the fact that in the former reaction solution, the amounts of impurities contained therein are high and they exert certain bad influences during the concentration by heating.

In the practice of this invention, the hydration reaction is carried out by bringing acrylonitrile into contact with the microorganism or enzyme, which is, if desired, immobilized, in an aqueous medium in such a manner that the concentration of acrylamide after the reaction be from 5% by weight to less than 20% by weight, and preferably from 5% by weight to 15% by weight.

The reaction temperature is usually from the freezing point to 30° C., more preferably from the freezing point to 15° C.

The pH is adjusted to a range of from 6 to 10, and preferably from 7 to 9, if necessary, by adding hydroxides, carbonates, bicarbonates, phosphates, borates and organic acid salts of alkali metals, hydroxides of alkaline earth metals or the like.

In order to improve the enzyme activity, small amounts of magnesium ions, calcium ions, etc. can be incorporated in the reaction solution.

The pressure exerts no appreciable influence on the hydration reaction. Thus, the hydration reaction can be carried out at a pressure range of from 0.1 to 10 kg/cm$^2$. Preferably it is carried out in the vicinity of atmospheric pressure. However, if the pressure is exceedingly low, undesirable vaporization of acrylonitrile occurs, and the gases dissolved in the reaction solution are liberated as bubbles, attaching to the surface of the enzyme-containing material and preventing the solid-liquid contact. Therefore, it is preferred to previously deaerate the reaction solution, particularly if the reaction is carried out under low pressure conditions. The deaeration can easily be conducted by a flash evaporation, for example, under pressure of 0.05 to 0.7 kg/cm$^2$.

The water for use in the hydration reaction is preferably pure water, and the concentration of oxygen dissolved therein may be from 0.5 ppm to saturation. When the concentration of the dissolved oxygen is less than 0.5 ppm, since the polymerization of acrylamide easily occur during the reaction, such concentration is not preferred.

The reactor used in the practice of this invention may be of the known fixed bed type, moving bed type, suspension bed type reactors of the solid-liquid system, etc. As a suspension bed type reactor, a stirring vessel type reactor can be used, but fluidized bed type, floating bed type (U.S. Pat. No. 3,288,567) and spouting bed type reactors are preferably used, because they cause less fracture of the immobilized microorganisms or enzyme. Where the microorganism strain is used as is, it is preferred to use a stirring vessel type reactor. Usually one, two or more reactors are connected in series. Where two or more reactors are used, or the moving bed type reactor is used, the amount of the microorganism or enzyme being used can be reduced by countercurrently or cocurrently contacting the reaction solution with the microorganism or enzyme.

The reaction solution obtained by the hydration reaction is then concentrated. If necessary, the solids in the reaction solution are removed by filtration and precipitation before the treatment of concentration. This concentration of the reaction solution can be carried out by any known method. In the method of this invention, however, it is preferred that the freezing concentration method is first applied, and the solution so concentrated is, if desired, further concentrated by another method.

In the freezing concentration, the concentration of acrylamide in the reaction solution concentrated is about 31% by weight or less, preferably 28% by weight or less. As a method of further concentrating the solution so concentrated, for instance, the method of removing water by evaporation thereof under reduced pressure can be employed. In this evaporating concentration, the aqueous solution of acrylamide can be obtained in concentration of about 80% by weight or less, preferably 60% by weight or less. Further, in the evaporating concentration, it is desirable to employ the oxygen and air as a polymerization inhibitor. Since unreacted acrylonitrile is formed in the evaporating concentration, this unreacted acrylonitrile is recovered and can be used in the hydration reaction.

The freezing concentration method is described in more detail below.

The freezing concentration method is a method wherein an aqueous solution is concentrated by crystallizing ice out of the aqueous solution, and separating the ice from the aqueous solution. The crystallization of ice can be carried out by: (1) a method in which the reaction solution is cooled by brine; (2) a method in which the reaction solution is cooled by heat of evaporation of liquid freon or liquid ammonia; (3) a method in which the reaction solution is brought in direct contact with liquid butane or liquid butene; (4) a method in which the reaction solution is cooled by evaporating the water contained therein under a highly reduced pressure of about 1 mmHg; and so forth. For obtaining a high concentrated acrylamide aqueous solution, it is necessary to control the cooling temperature to $-4°$ C. or less. Since acrylamide and water form an eutectic mixture containing about 31% by weight of acrylamide at about $-9°$ C., the crystallization temperature is preferably from about $-4°$ C. to $-9°$ C.

The ice so obtained is separated by filtration or a floating method. Preferably the ice is separated from the acrylamide aqueous solution by centrifugal filtration and the ice is, if necessary, washed with water. The ice so crystallized and separated is then used, as described above, for the removal of the heat of the hydration reaction. Where the amount of the ice formed is excessive than the amount of the ice needed for cooling in the hydration reaction, it is heated with hot water to melt a part thereof and then it is supplied to the hydration step or withdrawn as waste water. On the other hand, when the amount of the ice formed is about 4 kg based on 1 kg of acrylamide, there are instances where the amount of the ice lacks. In such cases, it is also required in the hydration reaction to cool with the freezer.

While the heat of hydration of acrylonitrile is as great as about 17 Kcal/mol and thus the removal of heat is of importance to the low temperature reaction of this invention, the removal of heat can easily be achieved by using the above formed ice for the cooling. In particular, it is preferred to bring a feed mixture of acrylonitrile, water and an enzyme-containing material and the reaction solution into direct contact with the ice, since they can thereby be easily cooled to near the freezing point. The removal of the heat of hydration can also be indirectly carried out with the ice obtained by the freezing concentration by use of a heat exchanger or a shell and tube type reactor. In this case, the melted ice is, as necessary, used as a feed for the hydration reaction or a medium.

The process of this invention will now be described by way of example with reference to the accompanying drawing.

The FIGURE is a diagram showing an embodiment of the process of this invention. A cooler 4 is an apparatus wherein a reaction solution and ice are brought in direct contact with each other and separated from each other by buoyancy and filtration. In this cooler 4, acrylonitrile and water introduced through conduits 1 and 2, respectively, and reaction solution returned through a conduit 6 from a first reactor 8 are cooled by ice introduced through a conduit 3. The solution so cooled is sent through a conduit 7 to the first reactor 8 by use of a circulating pump 5. The first reactor 8 is a fixed bed type reactor which is filled with immobilized strains. A part of the reaction solution withdrawn from the first reactor 8 is sent through a conduit 9 to a second reactor 10 which is also a fixed bed type reactor filled with immobilized strains. The reaction solution withdrawn from the second reactor 10 is sent through a conduit 11 to a crystallization vessel 12 wherein it is cooled by a cooling medium 13 to crystallize ice. An ice slurry is introduced through a conduit 14 to a centrifugal separator 15 wherein it is separated into solids and liquid. A part of the liquid is returned through a conduit 16 to the crystallization vessel 12, and the remainder is withdrawn as a concentrated acrylamide aqueous solution through a conduit 17 and employed as a product as it is or after being concentrated by heating under reduced pressure. The ice slurry is sent through the conduit 3 to the cooler 4 wherein it is used for the cooling of the reaction solution and as a feed or a medium for the hydration.

The highly concentrated aqueous solution of acrylamide obtained by this invention can be used as it is as a starting material for the production of various polymers. From this aqueous solution, acrylamide can be obtained as crystals by known crystallization techniques.

The following examples are given to illustrate this invention in greater detail. All parts and percents are by weight.

EXAMPLE 1

Strain N-774 was aerobically incubated on a medium (pH 7.2) containing 1% of glucose, 0.5% of peptone, 0.3% of yeast extract, and 0.3% of wheat extract. The washed strain of Strain N-774 (containing 75% water) in an amount of 40 parts was mixed with 4.5 parts of acrylamide, 0.5 part of N,N'-methylenebisacrylamide and 40 parts of an isotonic sodium chloride solution to prepare a uniform suspension. To this suspension were added 5 parts of a 5% aqueous solution of dimethylaminopropionitrile and 10 parts of a 25% aqueous solution of potassium persulfate, and the resulting mixture was polymerized while maintaining at 10° C. for 30 minutes. The thus-obtained massive strain-containing gel was pulverized into small particles and throughly washed with an isotonic sodium chloride solution to obtain 100 parts of an immobilized strain.

By using the immobilized strain as obtained above, a hydration reaction and concentration were conducted according to the method with the diagram as illustrated in the figure.

Firstly, each of a first reactor 8 and a second reactor 10 was charged with 40 parts of the above obtained immobilized strain. A cooler 4 and a crystallization vessel 12 were charged with water with a pH of 8, and the first reactor 8 and the second reactor 10 were charged with water with a pH of 8. Then, to the cooler 4 were introduced 20 parts/hr of an aqueous solution of acrylonitrile at a pH of 8, in which 4.5 parts/hr of a 0.1% aqueous solution of acrylic acid was neutralized with an aqueous solution of sodium carbonate, and 16 parts/hr of ice. The solution cooled in the cooler 4 was sent to the first reactor 8 in the amount of 200 parts/hr by use of a circulating pump 5. Of the effluent from the first reactor 8, 160 parts/hr was returned to the cooler 4, and the remainder of 40 parts/hr was introduced into the second reactor 10. The effluent from the second reactor 10 was introduced into a crystallization vessel 12 wherein it was cooled by brine. The ice slurry thus obtained was separated in a centrifugal separator, and 21 parts/hr of the liquid obtained was withdrawn and the remainder was returned to the crystallization vessel 12. Ice was formed in the amount of 16 parts/hr, which was supplied to the cooler 4.

When the reaction become nearly constant, the temperature in the cooler 4 was −4° C., the temperature in the outlet of the second reactor was 3° C., and the temperature in the crystallization vessel 12 was −8° C. The concentration of acrylamide in the effluent from the second reactor 10 was 15%, and the concentration of acrylamide in the concentrated solution withdrawn from the conduit 17 was 28%.

In order to confirm the quality of the thus-obtained acrylamide aqueous solution, the following test was conducted:

A polymerization reactor was charged with 657 g of the above concentrated acrylamide solution (concentration 28%) and 119 g of ion exchanged water, and 4.8 g of boric acid and 3.2 g of caustic soda were added thereto as hydrolyzing agents. Then the air in the polymerization reactor was completely replaced by a nitrogen gas, and 32 mg of potassium persulfate and 32 mg of dimethylaminopropionitrile were each dissolved in 10 ml of water at 25° C. and added. After the induction period of about 15 minutes, the polymerization abruptly proceeded, and in about 90 minutes the maximum temperature was reached. After further keeping at 90° C. for 16 hours, the gel-like polymer was pulverized and dried with hot air at 60° C. for 16 hours to obtain a dry product.

The viscosity of a 0.1% aqueous solution of the polymer (measured with a Brookfield type viscometer using a rotor No. 1 (6 rpm)) was about 700 cp, the hydrolysis ratio was 13 mole%, and the polymerization ratio was nearly 100%.

When the polymer was added in an amount of 0.5 to 1 ppm to waste water from the paper industry, which had been adjusted to a pH of from 6.5 to 7 by adding 30 to 50 ppm of aluminum sulfate, it exhibited markedly high aggregation capability.

EXAMPLE 2

In the same manner as in Example 1, Strain N-774 was incubated and immobilized. This immobilized strain in the amount of 100 parts was introduced into a stirring vessel type reactor and 900 parts of an aqueous solution with a pH of 8 which had been prepared by neutralizing a 0.1% aqueous solution of acrylic acid with an aqueous solution of sodium carbonate was added thereto. Then, while cooling at 5° C. from the outside with stirring, 80 parts of acrylonitrile was introduced therein over a period of 2 hours.

After the reaction was completed, the immobilized strain was filtered. The aqueous solution of acrylamide so obtained was 950 parts and the concentration of acrylamide was 10%.

This solution was cooled in the above reactor and then repeatedly subjected to a freezing concentration comprising crystallization of ice and a centrifugal operation. Thus, a 20% aqueous solution of acrylamide was obtained. This aqueous solution in the amount of 920 g was charged to a polymerization vessel, and in the same manner as in Example 1, a dry polymer was obtained. The results are shown in Table 1.

EXAMPLE 3

By carrying out the reaction and concentration in the same manner as in Example 2, except that the amount of acrylonitrile to be supplied was changed to 125 parts, a 20% aqueous solution of acrylamide and a dry acrylamide polymer were obtained. The results are shown in Table 1.

COMPARATIVE EXAMPLE 1

By carrying out the hydration reaction in the same manner as in Example 2, except that the amount of acrylonitrile to be supplied was increased to 173 parts, a 20% aqueous solution of acrylamide was obtained. Furthermore, this aqueous solution was processed in the same manner as in Example 2 to obtain a dry polymer. The results are shown in Table 1.

COMPARATIVE EXAMPLE 2

By carrying out only the hydration reaction in the same manner as in Example 2, except that the amount of acrylonitrile to be supplied was increased to 226 parts, a 25% aqueous solution of acrylamide was obtained. Furthermore, this aqueous solution was processed in the same manner as in Example 2 to obtain a dry polymer. The results are shown in Table 1.

EXAMPLE 4

Two jacketed fixed bed type reactors, each being charged with 40 parts of the immobilized Strain N-774 obtained in the same manner as in Example 1, were connected in series. An aqueous solution with a pH of 8 prepared by neutralizing a 0.1% aqueous solution of acrylic acid with sodium carbonate was introduced into a first reactor from the bottom thereof in an amount of 200 parts/hr. Of the effluent from the top of the first reactor, a portion of 160 parts/hr was returned to the first reactor and the remainder of 40 parts/hr was introduced into a second reactor from the top thereof. After cooling to 5° C. by flowing brine through the jacket of each reactor, 35.5 parts/hr of the aqueous solution in place of 40 parts/hr of the aqueous solution and 4.5 parts/hr of acrylonitrile were mixed with 160 parts/hr of the effluent from the top of the first reactor and the mixture so obtained was introduced into the first reactor from the bottom thereof in an amount of 200 parts/hr (SV ≈ 2 hr$^{-1}$). SV is the space velocity, which is defined by the equation.

$$SV\,(hr^{-1}) = \frac{\text{the feed rate (volume) per unit of time}}{\text{the volume of the reactor}}$$

The concentration of acrylamide in the effluent from the second reactor after the reaction reached the steady state was 15%.

The thus-obtained 15% aqueous solution of acrylamide was heated to 40° C. while blowing air therethrough, and sent to a flash evaporator wherein it was flash-evaporated and concentrated. To obtain a concentrated solution, the temperature of which lowered, and the same operation was repeated to obtain a 30% aqueous solution of acrylamide.

The thus-obtained solution was processed in the same manner as in Example 1 to obtain a dry polymer.

The polymerization smoothly proceeded. For the dry polymer obtained, the viscosity of a 0.1% aqueous solution thereof was about 700 cp and the hydrolysis ratio was 13 mole%. When this polymer was added in an amount of 0.5 to 1 ppm to waste water from the paper industry which had been adjusted to pH 6.5–7 by adding 30 to 50 ppm of aluminum sulfate, it exhibited good aggregation capability.

COMPARATIVE EXAMPLE 3

A mixture of 10 parts of a copper catalyst, 100 parts of acrylonitrile and 792 parts of water was charged to a reactor and subjected to a hydration reaction in the atmosphere of nitrogen at 100° C. for 8 hours. After the reaction was completed, the catalyst was separated. For the thus obtained reaction solution, the concentration of acrylamide was 15% and the amount of unreacted acrylonitril was 0.01%.

The reaction solution was introduced in a crystallization apparatus wherein it was gradually cooled with a cooling medium to −6° C. over a period of 4 hours. The resulting ice slurry was subjected to a centrifugal filtration, to obtain 647 parts of a 20% aqueous solution of acrylamide.

This concentrated solution was charged to a polymerization reactor wherein it was polymerized in the same manner as in Example 2, but even after a lapse of 4 hours no polymerization occurred.

TABLE 1

| | Example | | Comparative Example | |
|---|---|---|---|---|
| | 2 | 3 | 1 | 2 |
| Hydration Reaction | | | | |
| Amount of Acrylonitrile Supplied (parts) | 80 | 125 | 173 | 226 |
| Concentration of Acrylamide after Reaction (%) | 10 | 15 | 20 | 25 |
| Concentration | | | | |
| Concentration of Acrylamide after Concentration (%) | 20 | 20 | — | — |
| Polymerization Reaction | | | | |
| Temperature at the start of Polymerization (°C.) | 25 | 25 | 25 | 25 |
| Polymerization Period (min.) *1 | 90 | 90 | 100 | 110 |
| Characteristics of Polymer | | | | |
| Viscosity of 0.1% Aqueous Solution *2 (cp) | 700 | 700 | 600 | 500 |
| Hydrolysis Ratio *3 (mol %) | 13 | 13 | 13 | 13 |
| Aggregation Capability *4 (sec.) | 50–60 | 50–60 | 80–90 | 100 or more |

*1 Time required until the polymerization temperature reached the maximum.
*2 Measured by use of a Brookfield type viscometer (rotar No. 1, 6 rpm)
*3 Calculated from the data obtained by potentiometric titration using 0.1 N caustic soda.
*4 A measuring cylinder with a ground stopper, having a height of 25 cm and a volume of 100 ml, was charged with a 5% suspension of clay (Tsuchiya Kaolin) and 0.3 ml of a 0.1% aqueous solution of the dry polymer. This measuring cylinder was turned upside down ten times and allowed to stand, and the time required for the flock interface to lower by 12.5 cm from the original position was measured. Smaller values indicate higher aggregation capabilities.

EXAMPLE 5

By carrying out the hydration reaction and concentration in the same manner as in Example 1, except that Strain N-771 was used in the place of Strain N-774, 28% aqueous solution of acrylamide was obtained. This obtained solution was polymerized and dried in the same manner as in Example 1 to obtain a dry polymer. For the dry polymer obtained, the viscosity of a 0.1% aqueous solution thereof was about 700 cp, the hydrolysis ratio was 13 mol% and the polymerization ratio was nearly 100%. When this polymer was added in an amount of 0.5 to 1 ppm to waste water from the paper industry which had been adjusted to pH 6.5–7 by adding 30 to 50 ppm of aluminum sulfate, it exhibited good aggregation capability.

EXAMPLE 6

By carrying out the hydration reaction and concentration in the same manner as in Example 2, except that Strain N-775 was used in the place of Strain N-774, 20% aqueous solution of acrylamide was obtained. 920 g of this obtained solution was charged to a polymerization reactor and then polymerized in the same manner as in Example 1 to obtain a dry polymer. For the dry polymer obtained, the viscosity of a 0.1% aqueous solution thereof was about 650 cp, the hydrolysis ratio was 13 mol% and the polymerization ratio was nearly 100%. When the polymer was added in an amount of 0.5 to 1 ppm to waste water from the paper industry which had been adjusted to pH 6.5 to 7 by adding 30 to 50 ppm of aluminum sulfate, it exhibited good aggregation capability.

While the invention has been described in detail and with reference to specific embodiments thereof, it will be apparent to one skilled in the art that various changes and modifications can be made therein without departing from the spirit and scope thereof.

What is claimed is:

1. A process for producing acrylamide from acrylonitrile by utilizing a microorganism or enzyme capable of hydrating acrylonitrile into acrylamide in the form of a highly concentrated aqueous acrylamide solution, comprising bringing acrylonitrile in contact with the microorganism or enzyme in an aqueous medium at a pH of from 6 to 10, at a temperature of from the freezing point to 30° C., and under such conditions that the concentration of acrylamide in the reaction solution after completion of the reaction is from 5% by weight to less than 20% by weight, and concentrating the resulting reaction solution by freezing and/or evaporation, wherein the reaction solution is concentrated to about 31% by weight or less of acrylamide by cooling the reaction solution after the end of the reaction to a temperature of from −4° C. to −9° C. to crystallize ice, separating the crystallized ice, and using the separated ice for cooling during the hydration reaction and wherein said process additionally includes using the ice and melted ice for a feed for the hydration reaction as a component of the aqueous medium.

2. A process as in claim 1, wherein the hydration reaction is carried out at a temperature of from the freezing point to 15° C.

3. A process as in claim 1, wherein the concentrated solution obtained by the crystallization of the reaction solution following by the separation of the crystallized ice is further concentrated to about 80% by weight or less of acrylamide by removing water by the evaporation thereof.

4. A process as in claim 1, wherein the concentration of acrylamide in the reaction solution concentrated is 28% by weight or less.

5. A process as in claim 3, wherein the concentration of acrylamide in the further concentrated solution is 60% by weight or less.

6. A process as in claim 1, wherein the microorganism is selected from the group consisting of the genera Bacillus, Bacteridium, Micrococcus, Brevibacterium, Corynebacterium and Nocardia.

7. A process as in claim 1, wherein the microorganism is selected from the group consisting of the genera Corynebacterium and Nocardia.

8. A process as in claim 7, wherein the microorganism is selected from the group consisting of Strains N-771, N-774 and N-775.

9. A process as in claim 1, wherein the microorganism strain is immobilized on a polyacrylamide based gel.

10. A process as in claim 1, wherein the pH is from 7 to 9.

11. A process as in claim 1, wherein the concentration of acrylamide in the reaction solution after completion of the reaction is from 5% by weight to 15%.

* * * * *